United States Patent [19]

D'Alessio et al.

[11] Patent Number: 5,847,127
[45] Date of Patent: Dec. 8, 1998

[54] PROCESS FOR THE PREPARATION OF 2,2'-BIPYRROLYL-PYRROMETHENE (PRODIGIOSINS) DERIVATIVES

[75] Inventors: Roberto D'Alessio, Cinisello Balsamo; Arsenia Rossi, Dalmine; Marcellino Tibolla, Senago; Lucio Ceriani, Parabiago, all of Italy

[73] Assignee: Pharmacia & UpJohn S.p.A., Milan, Italy

[21] Appl. No.: 930,575

[22] PCT Filed: Jan. 22, 1997

[86] PCT No.: PCT/EP97/00368

§ 371 Date: Oct. 15, 1997

§ 102(e) Date: Oct. 15, 1997

[87] PCT Pub. No.: WO97/30029

PCT Pub. Date: Aug. 21, 1997

[30] Foreign Application Priority Data

Feb. 15, 1996 [GB] United Kingdom ................... 9603212

[51] Int. Cl.[6] .................................................. C07D 413/04

[52] U.S. Cl. ........................... 544/141; 548/518; 548/519
[58] Field of Search ..................................... 548/518, 519; 544/141

[56] References Cited

FOREIGN PATENT DOCUMENTS

95/17381   6/1995   WIPO .

OTHER PUBLICATIONS

CA 13265–13268: Porphyrins. III. Preliminary studies on the synthesis of porphyrin a. Badger et al, 1964.

Journal of the Chemical Society. Porphyrins. Part I. Intramolecular Hydrogen Bonding in Pyrromethenes and Porphyrins. Badger et al, 1962.

*Primary Examiner*—Joseph K. McKane
*Attorney, Agent, or Firm*—Oblon, Spivak, McClelland, Maier & Neustadt, P.C.

[57] ABSTRACT

The present invention is related to a process for the preparation of 5-[2H-pyrrol-2-ylidene)methyl]-2,2'-bi-1H-pyrrole compounds and an intermediate compound.

6 Claims, No Drawings

PROCESS FOR THE PREPARATION OF 2,2'-BIPYRROLYL-PYRROMETHENE (PRODIGIOSINS) DERIVATIVES

This application is a 371 of PCT/EP97/00368 filed Jan. 22, 1997.

FIELD OF THE INVENTION

The present invention relates to a new process for the preparation of 5-[(2H-pyrrol-2-ylidene)methyl]-2,2'-bi-1H-pyrrole derivatives of formula (I):

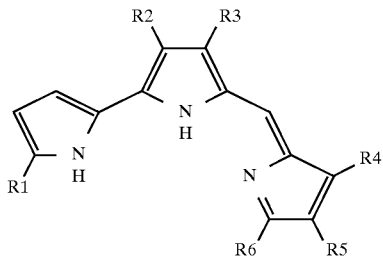

wherein
- R1 represents hydrogen, phenyl, $C_1$–$C_{20}$ alkyl or $C_2$–$C_{20}$ alkenyl, wherein the alkyl and alkenyl groups may be unsubstituted or substituted by 1 to 3 substituents chosen independently from halogen, $C_1$–$C_6$ alkoxy, hydroxy, aryl and aryloxy;
- R2 represents hydrogen, $C_1$–$C_6$ alkyl, cyano, carboxy or ($C_1$–$C_6$ alkoxy) carbonyl;
- R3 represents halogen, hydroxy or $C_1$–$C_{11}$ alkoxy unsubstituted or substituted by phenyl;
- R4 represent hydrogen, $C_1$–$C_6$ alkyl or phenyl;
- each of R5 and R6 independently represents hydrogen, $C_2$–$C_{20}$ alkanoyl, $C_3$–$C_{20}$ alkenoyl, phenyl, $C_1$–$C_{20}$ alkyl or $C_2$–$C_{20}$ alkenyl, wherein the alkanoyl, alkenoyl, alkyl and the alkenyl groups may be unsubstituted or substituted by 1 to 3 substituents chosen independently from halogen, $C_1$–$C_6$ alkoxy, hydroxy, aryl, aryloxy, cyano, carboxy, ($C_1$–$C_6$ alkoxy) carbonyl, ($C_3$–$C_4$ alkenyl) carbamoyl, aralkylcarbamoyl, arylcarbamoyl and -CONRcRd in which each of Rc and Rd independently is hydrogen or $C_1$–$C_6$ alkyl or Rc and Rd, taken together with the nitrogen atom to which they are linked, form a morpholino or piperidino ring;
- or two of R4, R5 and R6 taken together form a $C_4$–$C_2$ polymethylene chain, which can be unsubstituted or substituted by a $C_1$–$C_2$ alkyl, by a $C_2$–$C_{12}$ alkenyl or by a $C_1$–$C_{12}$ alkylidene group, wherein the alkyl, alkenyl and alkylidene groups may be in turn unsubstituted or substituted by a substituent chosen from halogen, $C_1$–$C_6$ alkoxy, hydroxy, cyano, carboxy, ($C_1$–$C_6$ alkoxy)carbonyl, aryloxy and aryl; the remaining one being hydrogen or $C_1$–$C_{12}$ alkyl; and the pharmaceutically acceptable salts thereof.

Several naturally occurring compounds having a 2,2'-bipyrrolyl-pyrromethene skeleton have been reported in literature: J. Antibiotics 24, 636 (1971); Mar. Biol. 34, 223 (1976); Can. J. Microbiol. 22, 658 (1976); Can. J. Chem. 56, 1155 (1978); Tetrahedron Letters 24, 2797 (1983); J. Antibiotics 38, 128 (1985), J. Gen. Microbiol. 132, 1899 (1986); J. Antibiotics 28, 194 (1975); Nature 213, 903 (1967); Tetrahedron Letters 24, 2701 (1983).

Most of the above references relates to compounds, generally known as 'prodigiosins', having antibiotic and cytotoxic properties.

More recently an immunosuppressive activity has been disclosed for some of them: J. Antibiotics 39, 1155 (1986); J6 1280 429-A; JO 2250 828-A; and for the synthetic ones WO 95/17381.

Most of the compounds known from such publications fall within the scope of formula (I) as defined above.

BACKGROUND OF THE INVENTION

Although some total synthesis of prodigiosins have been reported in the past years (Rapoport H., Holden K. J., J. Am. Chem. Soc. 84, 635 (1962); Boger D. L., Patel M., J. Org. Chem. 53, 1405 (1988); Wasserman H. H., Lombardo L. J., Tetrahedron Lett. 30, 1725 (1989); Wasserman H. H., Keith D. D., Nadelson J. Tetrahedron 32, 1867 (1976); Doria et al. WO 95/17381), most of prodigiosin derivatives known so far comes from natural source extraction.

The known synthetic methods for the preparations of prodigiosins in particular rely on:

a) condensation of a 2,2'-bipyrrole-aldehyde of general formula (II) with a substituted pyrrole (III) in acidic media:

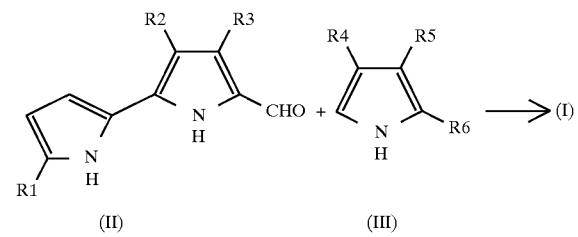

wherein
R1, R2, R3, R4, R5, R6 are as defined above; or b) condensation of a 2,2'-bipyrrole of general formula (IV) and a substituted pyrrole aldehyde (V):

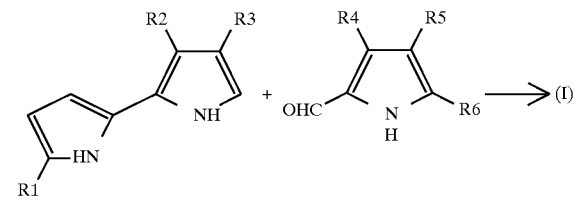

wherein
R1, R2, R3, R4, R5, R6 are as defined above.

Details of process-variants a) and b) can be found for instance in WO95/17381. However, in both processes the following main drawbacks can be noticed:

- the preparation of the 2,2'-bipyrrole key intermediates (II) and (IV) is time consuming and involves several steps (from 9 to 14).
- long lasting column chromatography purification are required.
- overall yields are not higher than 2.5%.

That makes the above-mentioned process not suitable to be scaled up. On the other hand, in view of the valuable biological properties of the compounds of formula (I), in particular of the immunomodulating compounds known from WO95/17381 encompassed therein, there is a need in this field of a process suitable for a large scale industrial production.

SUMMARY OF THE INVENTION

The present invention provides a new process for preparing a prodigiosin derivative of formula (I) as defined above, as shown in following Scheme 1:

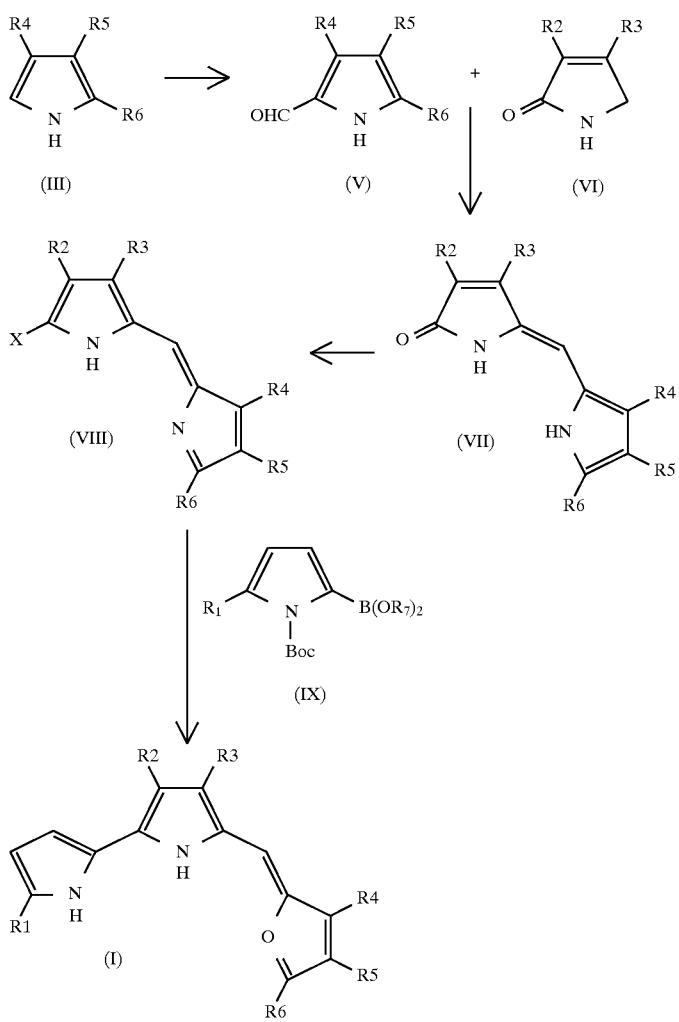

Scheme 1 wherein
R1, R2, R3, R4, R5, R6 are as defined above, R7 is hydrogen or a lower alkyl chain and X is a suitable leaving group.

This methodology involves the synthesis of the stable and easily obtainable pyrromethene fragment of general formula (VII), whereas the coupling to the 'left-hand' pyrrole ring to form the 2,2'-bipyrrole linkage is accomplished at the end.

Cross-coupling between pyrrole rings isn't a very common reaction. However, the reaction between a boronic acid of general formula (XI) and a opportunely activated dipyrromethene intermediate (VIII) resulted to be very effective for our purpose. This allowed us to get to the desired product in few steps and with very good yields, considering that Boc-deprotection occurred in the same reaction mixture. In fact, the all process consists in only four steps, and makes use of ready available starting materials. The overall yield is up to 30%.

The chemical compounds of formula (I) provided by the present invention are named throughout the description of the invention according to the chemical nomenclature provided for the same compounds in WO 95/17381.

A halogen atom is preferably chlorine or fluorine.

The alkyl, alkoxy, alkenyl, alkanoyl, alkenoyl, alkadienoyl and alkylidene groups may be branched or straight chain groups.

An aryl group as a substituent as well as a moiety in an aryloxy, aralkyl or arylcarbamoyl group is, e.g., an aromatic $C_6$–$C_{20}$ mono- or poly-nuclear moiety, typically phenyl, unsubstituted or substituted by one or two substituents independently chosen from halogen, hydroxy, $C_1$–$C_6$ alkyl and $C_1$–$C_6$ alkoxy.

Accordingly an aralkyl group is e.g. benzyl or phenethyl, in which the phenyl ring is optionally substituted by one or two substituents independently chosen from halogen, hydroxy, $C_1$–$C_6$ alkyl and $C_1$–$C_6$ alkoxy.

A $C_4$–$C_2$ polymethylene chain is e.g. a $C_4$–$C_9$ polymethylene chain.

A $C_3$–$C_4$ or $C_3$–$C_6$ alkenyl group is preferably an allyl group.

A $C_1$–$C_6$ alkyl group is preferably a $C_1$–$C_4$ alkyl group, in particular a methyl or ethyl group.

A $C_1$–$C_{12}$ alkyl group is preferably a $C_1$–$C_6$ alkyl group.

An unsubstituted $C_1$–$C_{11}$ alkoxy group is preferably a $C_1$–$C_5$ alkoxy or $C_8$–$C_{11}$ alkoxy group, typically methoxy, ethoxy, propoxy, butoxy, amyloxy and undecyloxy.

A $C_1$–$C_6$ alkoxy group substituted by phenyl is preferably a phenyl-$C_1$–$C_4$ alkoxy group, typically benzyloxy or phenylethoxy.

A $C_1$–$C_{20}$ alkyl group is preferably a $C_5$–$C_{14}$ alkyl group, in particular an undecyl group.

A $C_2$–$C_{20}$ alkenyl group is preferably a $C_5$–$C_{14}$ alkenyl group, in particular an undecenyl group.

A $C_2$–$C_{20}$ alkanoyl group is preferably a $C_5$–$C_{14}$ alkanoyl group, in particular an undecanoyl group.

A $C_3$–$C_{20}$ alkenoyl group is preferably a $C_5$–$C_{14}$ alkenoyl group, in particular an undecenoyl group.

A $C_1$–$C_{12}$ alkylidene group is preferably a $C_1$–$C_8$ alkylidene group, in particular a $C_4$–$C_6$ alkylidene group.

A $C_2$–$C_{12}$ alkenyl group is preferably a $C_3$–$C_6$ alkenyl group.

A ($C_1$–$C_6$ alkoxy)carbonyl group is preferably a ($C_1$–$C_4$ alkoxy) carbonyl group.

Examples of pharmaceutically acceptable salts are either those with inorganic bases, such as sodium, potassium, calcium and aluminium hydroxides, or with organic bases, such as lysine, arginine, N-methyl-glucamine, triethylamine, triethanolamine, dibenzylamine, methylbenzylamine, di-(2-ethyl-hexyl)-amine, piperidine, N-ethylpiperidine, N,N-diethylaminoethylamine, N-ethylmorpholine, β-phenethylamine, N-benzyl-β-phenethylamine, N-benzyl-N,N-dimethylamine and the other acceptable organic amines, as well as the salts with inorganic, e.g. hydrochloric, hydrobromic and sulphuric acids and with organic acids, e.g. citric, tartaric, maleic, malic, fumaric, methanesulphonic and ethanesulphonic acids.

Preferred compounds of the invention are the compounds of formula (I) wherein

R1 represents hydrogen, $C_1$–$C_{12}$ alkyl or $C_2$–$C_{12}$ alkenyl, wherein the alkyl and the alkenyl groups may be unsubstituted or substituted by aryl or aryloxy;

R2 represents hydrogen, cyano, carboxy or ($C_1$–$C_4$ alkoxy) carbonyl;

R3 represents hydroxy or $C_1$–$C_{11}$ alkoxy unsubstituted or substituted by phenyl;

R4 represents hydrogen or $C_1$–$C_4$ alkyl;

each of R5 and R6 independently represents hydrogen, $C_3$–$C_{14}$ alkyl or $C_3$–$C_{14}$ alkenyl, wherein the alkyl and the alkenyl groups may be unsubstituted or substituted by a substituent chosen from halogen, $C_1$–$C_4$ alkoxy, hydroxy, aryl, aryloxy, cyano, carboxy, ($C_1$–$C_4$ alkoxy)carbonyl, aralkylcarbamoyl, arylcarbamoyl and -CONRcRd in which each of Rc and Rd independently is hydrogen or $C_1$–$C_4$ alkyl or Rc and Rd, taken together with the nitrogen atom to which they are linked, form a morpholino or piperidino ring; or two of R4, R5 and R6 taken together form a $C_4$–$C_9$ polymethylene chain, which can be unsubstituted or substituted by a $C_1$–$C_6$ alkyl, by a $C_3$–$C_6$ alkenyl or by a $C_1$–$C_8$ alkylidene group, wherein the alkyl, alkenyl and alkylidene groups may be in turn unsubstituted or substituted by a substituent chosen from halogen, $C_1$–$C_4$ alkoxy, hydroxy, cyano, carboxy, ($C_1$–$C_4$ alkoxy)carbonyl, aryloxy and aryl; the remaining one being hydrogen or $C_1$–$C_6$ alkyl; and the pharmaceutically acceptable salts thereof.

Examples of particularly preferred compounds of the invention are:

4-methoxy-5-[(5-undecyl-2H-pyrrol-2-ylidene)methyl]-2,2'-bi-1H-pyrrole;
4-ethoxy-5-[[5-(undec-10-en-1-yl)-2H-pyrrol-2-ylidene] methyl]-2,2'-bi-1H-pyrrole;
4-ethoxy-5-[(5-decyl-2H-pyrrol-2-ylidene)methyl]-2,2'-bi-1H-pyrrole;
4-ethoxy-5-[(5-dodecyl-2H-pyrrol-2-ylidene)methyl]-2,2'-bi-1H-pyrrole;
4-ethoxy-5-[(5-phenethyl-2H-pyrrol-2-ylidene)methyl]-2,2'-bi-1H-pyrrole;
4-ethoxy-5-[[5-(5-phenoxy-pent-1-yl)-2H-pyrrol-2-ylidene] methyl]-2,2'-bi-1H-pyrrole;
4-ethoxy-5-[(5-tridecyl-2H-pyrrol-2-ylidene)methyl]-2,2'-bi-1H-pyrrole;
4-ethoxy-5-[(5-methyl-2H-pyrrol-2-ylidene)methyl]-2,2'-bis-1H-pyrrole;
4-amyloxy-5-[(5-undecyl-2H-pyrrol-2-ylidene)methyl]-2,2'-bi-1H-pyrrole;
4-undecyloxy-5-[(5-undecyl-2H-pyrrol-2-ylidene)methyl]-2,2'-bi-1H-pyrrole;
4-undecyloxy-5-[(2H-pyrrol-2-ylidene)methyl]-2,2'-bi-1H-pyrrole;
4-buthoxy-5-[(5-tridecyl-2H-pyrrol-2-ylidene)methyl]-2,2'-bi-1H-pyrrole;
4-benzyloxy-5-[(5-tridecyl-2H-pyrrol-2-ylidene)methyl]-2,2'-bi-1H-pyrrole;
4-buthoxy-5-[[5-(5-phenoxy-pent-1-yl)-2H-pyrrol-2-ylidene] methyl)-2,2'-bi-1H-pyrrole;
4-benzyloxy-5-[[5-(5-phenoxy-pent-1-yl)-2H-pyrrol-2-ylidene] methyl]-2,2'-bi-1H-pyrrole;
4-propoxy-5-[(5-undecyl-2H-pyrrol-2-ylidene)methyl]-2,2'-bi-1H-pyrrole;
4-butoxy-5-[(5-undecyl-2H-pyrrol-2-ylidene)methyl]-2,2'-bi-1H-pyrrole;
4-isopropoxy-5-[(5-undecyl-2H-pyrrol-2-ylidene)methyl]-2,2'-bi-1H-pyrrole;
4-propoxy-5-[(5-decyl-2H-pyrrol-2-ylidene)methyl]-2,2'-bi-1H-pyrrole;
4-propoxy-5-[(5-dodecyl-2H-pyrrol-2-ylidene)methyl]-2,2'-bi-1H-pyrrole;
4-propoxy-5-[[5-(undec-10-en-1-yl)-2H-pyrrol-2-ylidene] methyl]-2,2'-bi-1H-pyrrole;
4-propoxy-5-[[5-(5-phenoxy-pent-1-yl)-2H-pyrrol-2-ylidene] methyl]-2,2'-bi-1H-pyrrole;
4-benzyloxy-5-[(5-undecyl-2H-pyrrol-2-ylidene)methyl]2,2'-bi-1H-pyrrole;
4-benzyloxy-5-[(2H-pyrrol-2-ylidene)methyl]-2,2'-bi-1H-pyrrole;
4-methoxy-5-[[5-(7-cyano-hept-1-yl)-2H-pyrrol-2-ylidene] methyl]-2,2'-bi-1H-pyrrole;
4-methoxy-5-[[5-(undec-10-en-1-yl)-2H-pyrrol-2-ylidene] methyl]-2,2'-bi-1H-pyrrole;
4-methoxy-5-[(5-decyl-2H-pyrrol-2-ylidene)methyl]-2,2'-bi-1H-pyrrole;
4-methoxy-5-[(5-dodecyl-2H-pyrrol-2-ylidene)methyl]-2,2'-bi-1H-pyrrole;
4-methoxy-5-[(5-tridecyl-2H-pyrrol-2-ylidene)methyl]-2,2'-bi-1H-pyrrole;
4-methoxy-5-[(5-pentadecyl-2H-pyrrol-2-ylidene)methyl]-2,2'-bi-1H-pyrrole;
4-methoxy-5-[(5-propyl-2H-pyrrol-2-ylidene)methyl]-2.2'-bi-1H-pyrrole;
4-methoxy-5-[(5-heptyl-2H-pyrrol-2-ylidene)methyl]-2,2'-bi-1H-pyrrole;
4-methoxy-5-[(5-phenethyl-2H-pyrrol-2-ylidene)methyl]-2,2'-bi-1H-pyrrole;
4-methoxy-5-[(5-methyl-4-undecyl-2H-pyrrol-2-ylidene) methyl]-2,2'-bi-1H-pyrrole;
4-methoxy-5-[(5-propyl-4-undecyl-2H-pyrrol-2-ylidene) methyl]-2,2'-bi-1H-pyrrole;
4-methoxy-5-[[5-(5-phenoxy-pent-1-yl)-2H-pyrrol-2-ylidene] methyl]-2,2'-bi-1H-pyrrole;
4-methoxy-5-[(4-ethyl-3,5-dimethyl-2H-pyrrol-2-ylidene) methyl]-2,2'-bi-1H-pyrrole;
4-methoxy-5-[(4-hexyl-5-methyl-2H-pyrrol-2-ylidene) methyl]-2,2'-bi-1H-pyrrole;
4-methoxy-5-[(5-nonyl-2H-pyrrol-2-ylidene)methyl]-2,2'-bi-1H-pyrrole;
4-methoxy-5-[(5-methyl-4-pentyl-2H-pyrrol-2-ylidene) methyl]-2,2'-bi-1H-pyrrole;

4-methoxy-5-[[5-(5-carboxy-pent-1-yl)-2H-pyrrol-2-ylidene] methyl]-2,2'-bi-1H-pyrrole;
4-methoxy-5-[[5-(5-carboxy-pent-1-yl)-2H-pyrrol-2-ylidene] methyl]-2,2'-bi-1H-pyrrole, methyl ester;
4-methoxy-5-[[5-(6-hydoxy-hex-1-yl)-2H-pyrrol-2-ylidene] methyl]-2,2'-bi-1H-pyrrole;
4-methoxy-5-[[5-(6-fluoro-hex-1-yl)-2H-pyrrol-2-ylidene] methyl]-2,2'-bi-1H-pyrrole;
4-methoxy-5-[[5-(5-morpholinecarboxamido-pent-1-yl)-2H-pyrrol-2-ylidene]methyl]-2,2'-bi-1H-pyrrole;
4-ethoxy-5-[(5-ethyl-4-pentyl-2H-pyrrol-2-ylidene)methyl]-2,2'-bi-1H-pyrrole;
4-ethoxy-5-[(5-methyl-4-pentyl-2H-pyrrol-2-ylidene) methyl]-2,2'-bi-1H-pyrrole;
4-ethoxy-5-[(5-ethyl-4-undecyl-2H-pyrrol-2-ylidene) methyl]-2,2'-bi-1H-pyrrole;
4-ethoxy-5-[(5-methyl-4-undecyl-2H-pyrrol-2-ylidene) methyl]-2,2'-bi-1H-pyrrole;
4-ethoxy-5-[(5-heptyl-4-undecyl-2H-pyrrol-2-ylidene) methyl]-2,2'-bi-1H-pyrrole;
4-propoxy-5-[(5-ethyl-4-undecyl-2H-pyrrol-2-ylidene) methyl)-2,2'-bi-1H-pyrrole;
4-ethoxy-5-[(4-ethyl-3,5-dimethyl-2H-pyrrol-2-ylidene) methyl]-2,2'-bi-1H-pyrrole;
4-ethoxy-5-[[5-(5-carboxy-pent-1-yl)-2H-pyrrol-2-ylidene] methyl]-2,2'-bi-1H-pyrrole;
4-propoxy-5-[[5-(5-carboxy-pent-1-yl)-2H-pyrrol-2-ylidene] methyl]-2,2'-bi-1H-pyrrole;
4-ethoxy-5-[[5-(6-hydroxy-hex-1-yl)-2H-pyrrol-2-ylidene] methyl]-2,2'-bi-1H-pyrrole;
4-propoxy-5-[[5-(6-hydroxy-hex-1-yl)-2H-pyrrol-2-ylidene] methyl]-2,2'-bi-1H-pyrrole;
4-propoxy-5-[[5-(11-carboxy-undec-1-yl)-2H-pyrrol-2-ylidene] methyl]-2,2'-bi-1H-pyrrole;
4-propoxy-5-[[5-(12-carboxy-dodec-1-yl)-2H-pyrrol-2-ylidene] methyl]-2,2'-bi-1H-pyrrole;
4-propoxy-5-[[5-(12-hydroxy-dodec-1-yl)-2H-pyrrol-2-ylidene] methyl]-2,2'-bi-1H-pyrrole;
4-propoxy-5-[[5-(13-hydroxy-tridec-1-yl)-2H-pyrrol-2-ylidene] methyl]-2,2'-bi-1H-pyrrole;
4-propoxy-5-[[5-(11-cyano-undec-1-yl)-2H-pyrrol-2-ylidene] methyl]-2,2'-bi-1H-pyrrole; 4-propoxy-5-[[5-(11-carbamoyl-undec-1-yl)-2H-pyrrol-2-ylidene]methyl]-2,2'-bi-1H-pyrrole;
4-propoxy-5-[[5-(11-ethoxycarbonyl-undec-1-yl)-2H-pyrrol-2-ylidene]methyl]-2,2'-bi-1H-pyrrole;
4-ethoxy-5-[(5-undecanoyl-2H-pyrrol-2-ylidene)methyl]-2,2'-bi-1H-pyrrole;
4-ethoxy-5-[[5-(11-carboxy-undec-1-yl)-2H-pyrrol-2-ylidene] methyl)-2,2'-bi-1H-pyrrole;
4-ethoxy-5-[[5-(12-carboxy-dodec-1-yl)-2H-pyrrol-2-ylidene] methyl]-2,2'-bi-1H-pyrrole;
4-ethoxy-5-[[5-(12-hydroxy-dodec-1-yl)-2H-pyrrol-2-ylidene] methyl]-2,2'-bi-1H-pyrrole;
4-ethoxy-5-[[5-(13-hydroxy-tridec-1-yl)-2H-pyrrol-2-ylidene] methyl]-2,2'-bi-1H-pyrrole;
4-ethoxy-5-[[5-(11-cyano-undec-1-yl)-2H-pyrrol-2-ylidene] methyl]-2,2'-bi-1H-pyrrole;
4-ethoxy-5-[[5-(11-carbamoyl-undec-1-yl)-2H-pyrrol-2-ylidene] methyl]-2,2'-bi-1H-pyrrole;
4-ethoxy-5-[[5-(11-ethoxycarbonyl-undec-1-yl)-2H-pyrrol-2-ylidene]methyl]-2,2'-bi-1H-pyrrole;
4-methoxy-5-[(4,5,6,7-tetrahydro-2H-indol-2-ylidene) methyl]-2,2'-bi-1H-pyrrole;
4-methoxy-5-[(4-hexyl-4,5,6,7-tetrahydro-2H-indol-2-ylidene) methyl]-2,2'-bi-1H-pyrrole;
4-ethoxy-5-[(4-hexyl-4,5,6,7-tetrahydro-2H-indol-2-ylidene) methyl]-2,2'-bi-1H-pyrrole;
4-propoxy-5-[(4-hexyl-4,5,6,7-tetrahydro-2H-indol-2-ylidene) methyl]-2,2'-bi-1H-pyrrole;
4-ethoxy-5-[[4-(4-carboxy-but-1-yl)-4,5,6,7-tetrahydro-2H-indol-2-ylidene]methyl]-2,2'-bi-1H-pyrrole;
4-ethoxy-5-[(3,5-nonamethylene-2H-pyrrol-2-ylidene) methyl]-2,2'-bi-1H-pyrrole;
4-propoxy-5-[(3,5-nonamethylene-2H-pyrrol-2-ylidene) methyl]-2,2'-bi-1H-pyrrole;
4-ethoxy-5-[[4-(4-ethoxycarbonyl-but-1-yl)-4,5,6,7-tetrahydro-2H-indol-2-ylidene]methyl]-2,2'-bi-1H-pyrrole;
4-ethoxy-5'-methyl-5-[(5-methyl-2H-pyrrol-2-ylidene) methyl- 2,2'-bi-1H-pyrrole;
4-propoxy-5'-methyl-5-[(5-undecyl-2H-pyrrol-2-ylidene) methyl]-2,2'-bi-1H-pyrrole;
4-ethoxy-5'-methyl-5-[[5-(undec-10-en-1-yl)-2H-pyrrol-2-ylidene]methyl]-2,2'-bi-1H-pyrrole;
4-ethoxy-5'-methyl-5-[(5-decyl-2H-pyrrol-2-ylidene) methyl]-2,2'-bi-1H-pyrrole;
4-ethoxy-5'-methyl-5-[(5-dodecyl-2H-pyrrol-2-ylidene) methyl]-2,2'-bi-1H-pyrrole;
4-ethoxy-5'-methyl-5-[(3,5-nonamethylene-2H-pyrrol-2-ylidene) methyl]-2,2'-bi-1H-pyrrole;
4-ethoxy-5'-heptyl-5-[(5-undecyl-2H-pyrrol-2-ylidene) methyl)-2,2'-bi-1H-pyrrole;
4-ethoxy-5'-methyl-5-[(5-undecyl-2H-pyrrol-2-ylidene) methyl]-2,2'-bi-1H-pyrrole;
3-cyano-4-propoxy-5-[(5-undecyl-2H-pyrrol-2-ylidene) methyl]-2,2'-bi-1H-pyrrole;
3-cyano-4-ethoxy-5-[(5-undecyl-2H-pyrrol-2-ylidene) methyl]-2,2'-bi-1H-pyrrole;
3-cyano-4-ethoxy-5-[[5-(undec-10-en-1-yl)-2H-pyrrol-2-ylidene]methyl]-2,2'-bi-1H-pyrrole;
3-cyano-4-ethoxy-5'-methyl-5-[(5-undecyl-2H-pyrrol-2-ylidene)methyl]-2,2'-bi-1H-pyrrole;
3-ethoxycarbonyl-4-propoxy-5'-methyl-5-[(5-undecyl-2H-pyrrol-2-ylidene)methyl]-2,2'-bi-1H-pyrrole;
3-ethoxycarbonyl-4-ethoxy-5'-methyl-5-[(5-undecyl-2H-pyrrol-2-ylidene)methyl]-2,2'-bi-1H-pyrrole;
3-ethoxycarbonyl-4-ethoxy-5'-methyl-5-[[5-undec-10-en-1-yl-2H-pyrrol-2-ylidene]methyl]-2,2'-bi-1H-pyrrole;
3-methoxycarbonyl-4-methoxy-5'-methyl-5-[(5-undecyl-2H-pyrrol-2-ylidene)methyl]-2,2'-bi-1H-pyrrole;
3-ethoxycarbonyl-4-ethoxy-5'-methyl-5-[(3,5-nonamethylene- 2H-pyrrol-2-ylidene)methyl]-2,2'-bi-1H-pyrrole;
3-ethoxycarbonyl-4-ethoxy-5'-propyl-5-[(5-undecyl-2H-pyrrol-2-ylidene)methyl]-2,2'-bi-1H-pyrrole;
3-ethoxycarbonyl-4-propoxy-5'-methyl-5-[[5-(undec-10-en-1-yl) -2H-pyrrol-2-ylidene]methyl]-2,2'-bi-1H-pyrrole;
3-carboxy-4-propoxy-5'-methyl-5-[(5-undecyl-2H-pyrrol-2-ylidene)methyl]-2,2'-bi-1H-pyrrole;
3-carboxy-4-ethoxy-5'-methyl-5-[(5-undecyl-2H-pyrrol-2-ylidene)methyl]-2,2'-bi-1H-pyrrole;
3-carboxy-4-ethoxy-5'-methyl-5-[[5-(undec-10-en-1-yl)-2H-pyrrol-2-ylidene]methyl]-2,2'-bi-1H-pyrrole;
3-carboxy-4-ethoxy-5'-propyl-5-[(5-undecyl-2H-pyrrol-2-ylidene)methyl]-2,2'-bi-1H-pyrrole; and the pharmaceutically acceptable salts thereof.

DETAILED DESCRIPTION OF THE INVENTION

According to a preferred embodiment of the invention a compound of formula (I) and the salts thereof, as defined above, can be prepared by a process comprising the reaction of a compound of formula (VIII)

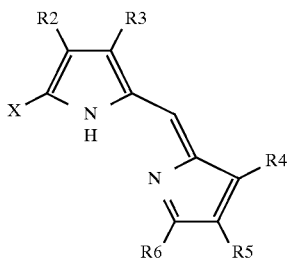

wherein
R2, R3, R4, R5, R6 are as defined above and X is a leaving group, with a compound of formula (IX)

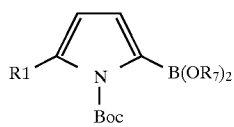

wherein
R1 is as defined above and R7 is hydrogen or a lower alkyl chain;
and, if desired, converting a compound of formula (I) into another compound of formula (I) and/or, if desired, salifying a compound of formula (I) and/or, if desired, converting a salt of a compound of formula (I) into a free compound and/or, if desired, separating a mixture of isomers of a compound of formula (I) into the single isomers.

When R7 is a lower alkyl chain, it is preferably a $C_1$–$C_4$ alkyl chain, for instance methyl, ethyl or isopropyl.

In a compound of general formula (VIII), the leaving group X can be for instance a trifluoromethanesulphonate group or a halogen such as chlorine, bromine or iodine.

The reaction between a compound of formula (VIII) and a compound of formula (IX) may be carried out in a suitable organic solvent such as tetrahydofurane, dioxane, dimethoxyethane, DMF, toluene, methanol, ethanol water or mixtures thereof, in the presence of a suitable palladium (0) catalyst, in the presence of a basic agent, such as $K_2CO_3$, $Na_2CO_3$, $NaHCO_3$, $K_3PO_4$, NaOAc, KOH, NaOH, Ba(OH)$_2$, EtONa, Bu$_4$NF, Et$_3$N, at a temperature varying between about 60° C. and about 120° C., for a time of about 1 hour to about 3 days.

A wide range of palladium (0) catalysts can be used such as for instance Pd(PPh$_3$)$_4$, PdCl$_2$(PPh$_3$)$_2$, Pd(OAc)$_2$ plus PPh$_3$ or other ligands as described for example in Chem. Rev. 95, 2457 (1995).

Optionally, salt such as LiCl, LiBr, KCl, KBr can be added to stabilize the catalyst.

According to a preferred embodiment of the invention, when in a compound of formula (VIII) the leaving group X is trifluoromethanesulfonate, a preferred catalyst is Pd(PPh$_3$)$_4$ in the presence of sodium or potassium carbonate, and the reaction can be performed in dioxane or toluene, at a temperature varying between about 65° C. and about 90° C., for a time from about 5 hours to about 24 hours.

A compound of formula (I) may be converted, as stated above, into another compound of formula (I) by known methods; for example, in a compound of formula (I) a carboxy group may be converted into the corresponding ($C_1$–$C_6$ alkyl)- or aryl-carbamoyl group by reaction with the suitable $C_1$–$C_6$ alkylamine or arylamine, respectively, in the presence of a suitable carbodiimide, such as dicyclohexyl-carbodiimide or 1-(3-dimethylamino-propyl)-3-ethyl-carbodiimide, in an inert solvent such as dichloromethane or tetrahydrofuran at a temperature varying between about 0° C. and about 30° C.

Also the optional salification of a compound of formula (I) as well as the conversion of a salt into the free compound and the separation of a mixture of isomers into the single isomers may be carried out by conventional methods. For example, the separation of optical isomers may be carried out by salification with an optically active base or acid and by subsequent fractional crystallization of the diastereoisomeric salts, followed by recovering of the optically active isomeric acids or, respectively, bases.

The compounds of formula (VIII) are novel compounds and are an object of the invention. A compound of formula (VIII) can be obtained from a compound of formula (VII)

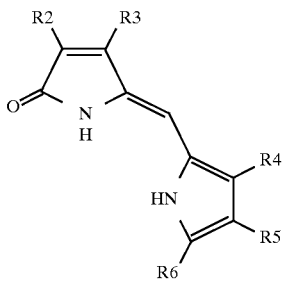

wherein
R2, R3, R4, R5, R6 are as defined above, by means of an opportune reagent such as for instance trifluoromethane-sulfonic anhydride or a halogenating agent such as POCl$_3$, POBr$_3$, POCl (OEt)$_2$/TMSI in an inert organic solvent such as dichloromethane, dichloroethane, acetonitrile, optionally in the presence of an organic base such as Et$_3$N or pyridine, at a temperature varying between about –20° C. and about –50° C.

The compounds of formula (IX) are known or can be prepared as described in published procedures, as for instance in Synthesis, 613 (1991).

The compounds of formula (VII) are novel compounds and are a further object of the present invention. They can be prepared reacting a compound of formula (V)

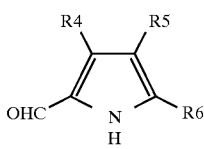

wherein
R4, R5, R6 are as defined above, with a compound of formula

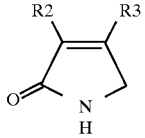

wherein
R2 and R3 are as defined above.

The condensation between a compound of formula (V) and a compound of formula (VI) can be performed by acidic or basic catalysis, in a solvent such as water, methanol, ethanol, dioxane, THF, DMF, DMSO or mixtures thereof, at a temperature varying from about 25° C. to about 12° C., in a time ranging from about 1 hour to about 24 hours.

A acidic catalyst can be e.g. an inorganic acid such as HCl, HBr, $H_2SO_4$, $H_2NO_3$ or an organic acid such as, for instance, p-toluensulphonic acid, methansulphonic acid, trifluoromethan-sulphonic acid or trifluoroacetic acid.

As well, a basic catalyst can be e.g. an inorganic base such as NaOH, KOH, $K_2CO_3$, $Ba(OH)_2$, NaH or an organic base such as, for instance, t-BuOk, MeLi, BuLi, LDA.

A compound of formula (VII) can be also converted in another compound of formula (VII) having a different R3 alkoxy group using well known chemical procedures conventionally used for the transesterification of organic esters.

The compounds of formula (V) can be prepared, for example, by Vilsmeier formylation of the compounds of formula (III)

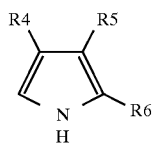
(III)

wherein R4, R5, R6 are as defined above, according to well known chemical procedures.

The compounds of formula (III) are known compounds or may be prepared using mere variations of published procedures, for example those reported in the following chemical literature:

Tetrahedron 32, 1851 (1976); Tetrahedron 32, 1867 (1976); Tetrahedron 32, 1863 (1976); Tetrahedron Letters 25, 1387 (1984); J.Org.Chem. 53, 1410 (1988); J.Org.Chem. 28, 857 (1963); J.Am.Chem.Soc. 84, 4655 (1962); Ann. 450, 181 (1926); Ber. 99, 1414 (1966).

The compound of formula (VI) are commercially available or can be synthesized as described for example in Synthesis, 391 (1992) and Tetrahedron Letters 25, 1871 (1984).

A compound of formula (VI) can be converted in another compound of formula (VI) having a different R3 alkoxy group, using well known chemical procedures conventionally used for the transesterification of organic esters.

When in the compounds of formula (I) and in the intermediate products thereof, groups are present, such as COOH and/or OH, which need to be protected before submitting them to the hereabove illustrated reactions, they may be protected before the reactions take place and then deprotected, according to well known methods in organic chemistry.

The following examples illustrate but do not limit the invention:

Example 1

Compound (VII)

To a solution of 2-formyl-5-undecylpyrrole (4 g; 16.03 mmols) and 4-methoxy-3-pyrrolin-2-one (3.63 g; 32.06 mmols) in DMSO (53 ml) 2N sodium hydroxyde (45 ml) is added under nitrogen atmosphere and the mixture is stirred at 60° C. for 8 hours. After dilution with water (200 ml) the yellow suspension is extracted with dichloromethane (600 ml). The organic phase is shacked with water and brine, anhydrified over anhydrous sodium sulphate and evaporated to dryness. The crude material is taken up in hexane and filtered to give 4-methoxy-5-(5-undecyl-1H-pyrrol-2-yl-methylene)-1,5-dihydro-pyrrol-2-one (4.86 g; 14.11 mmols) as a yellow crystalline solid. Yield: 88%.

$^1$NMR (400 mhz, $CDCl_3$), ppm: 0.87 (3H, m), 1.2–1.5 (16H, m), 1.72 (2H, m), 2.73 (2H, m), 3.89 (3H, s), 5.08 (1H, d, J=1.7 Hz), 5.97 (1H, dd, J=2.4 and 3.2 Hz), 6.31 (1H, s), 6.36 (1H, t, J=3.2 Hz), 10.25 (1H, bs), 10.74 (1H, bs).

Example 2

Compound (VIII)

To a solution of 4-methoxy-5-(5-undecyl-1H-pyrrol-2-yl-methylene)-1,5-dihydro-pyrrol-2-one (1 g; 2.90 mmols) in dichloromethane (50 ml) at 0–5° C. trifluoromethansulphonic anhydride (0.586 ml; 3.48 mmols) is added dropwise under nitrogen atmosphere. After stirring at this temperature for 30' the reaction mixture is poured into a 2% $NaHCO_3$ solution and extracted with ethyl acetate (2×50 ml). The collected organic extracts are shacked with brine, anhydrified over anhydrous sodium sulphate and evaporated to dryness. The crude material is chromatographed on a short column of silica gel eluting with hexane/ethyl acetate 85/15 to give 2-trifluoromethansulphonyloxy-4-methoxy-5-[(5-undecyl-2H-pyrrol-2-ylidene)methyl]-1H-pyrrole (980 mg; 2.06 mmols) as a yellow solid. Yield: 71%.

$^1$NMR (400 mhz, $CDCl_3$), ppm: 0.88 (3H, m), 1.1–1.6 (16H, m), 1.68 (2H, m), 2.70 (2H, m), 3.88 (3H, s), 5.45 (1H, s), 6.08 (1H, d, J=4.0 Hz), 6.70 (1H, d, J=4.0 Hz), 7.05 (1H, s), 10.9 (1H, bs).

Example 3

Interconversion Between Compounds (VI)

A solution of 4-methoxy-3-pyrrolin-2-one (3 g; 26.52 mmols) in absolute ethanol (60 ml) is treated with sodium ethoxyde (2.17 g; 31.82 mmols) under nitrogen atmosphere. The solution is refluxed for 2 hours and then poured into a 30% $NaH_2PO_4$ solution (200 ml) The resulting mixture is extracted with ethyl acetate (3×150 ml) and the organic phase is shacked with brine, dried over sodium sulphate and evaporated to dryness to obtain 4-ethoxy-3-pyrrolin-2-one (2.19 g; 17.24 mmols). Yield: 65%.

$^1$NMR (400 mhz, $CDCl_3$), ppm: 1.38 (3H, t), 3.89 (2H, s), 4.01 (2H, q), 5.03 (1H, s), 6.15 (1H, bs).

Example 4

Interconversion Between Compounds (VII)

A solution of 4-methoxy-5-(5-undecyl-1H-pyrrol-2-yl-methylene)-1,5-dihydro-pyrrol-2-one (190 mg; 1 mmol) in amyl alcohol (4.75 ml) and dioxane (4.75 ml) is treated with 0.25 N methansulphonic acid in dioxane (1 ml) and stirred at room temperature under nitrogen atmosphere for 6 hours. The mixture is then poured into water (50 ml) and extracted with ethyl acetate (3×30 ml). The organic phase is shacked with brine, dried over sodium sulphate and evaporated to dryness. The crude material is purified on silica gel eluting with ethyl acetate/methanol 98/2 to give 4-amyloxy-5-(5-undecyl-1H-pyrrol-2-yl-methylene)-1,5-dihydro-pyrrol-2-one (110 mg; 0.45 mmols). Yield: 45%.

$^1$NMR (400 mhz, $CDCl_3$), ppm: 0.91 (6H, m), 1.2–1.5 (20H, m), 1.72 (2H, m), 1.82 (2H, m), 2.73 (2H, m), 4.01 (2H, t), 5.08 (1H, d, J=1.7 Hz), 5.99 (1H, dd, J=2.4 and 3.2 Hz), 6.30 (1H, s), 6.36 (1H, t, J=3.2 Hz), 10.30 (1H, bs), 10.75 (1H, bs).

Example 5

Compound (I)

An oxygen free solution of 2-trifluoromethanesulphonyloxy-4-methoxy-5-[(5-undecyl- 2H-pyrrol-2-ylidene)methyl]-1H-pyrrole (418 mg; 0.877 mmols) in dioxane (30 ml) is treated in sequence, under argon atmosphere, with (1-t-buthoxycarbonylpyrrol-2-yl) boronic acid (740 mg; 3.51 mmols), potassium carbonate (969 mg; 7.02 mmols), tetrakis (triphenylphosphine) palladium(0) (50 mg; 0.044 mmols) and heated to 90° C., under stirring, for 6 hours. After cooling, the reaction mixture is poured into ice-water (100 ml) and extracted with ethyl acetate (3×50 ml). The organic phase is shacked with water and brine, anhydrified over anhydrous sodium sulphate, filtered and evaporated to dryness in vacuum. The residue is purified over a short $Al_2O_3$ column (activity II–III) using hexane/ethyl acetate 4/1 as eluant. The collected fractions are concentrated, treated with a solution of hydrochloric acid in isopropyl ether and evaporated to dryness in vacuum at room temperature to give 4-methoxy-5-[(5-undecyl-2H-pyrrol-2-ylidene)methyl]-2,2'-bi-1H-pyrrole, hydrochloride (275 mg; 0.640 mmols), m.p. 92°–95° C. Yield: 73%.

$^1$NMR (400 mhz, $CDCl_3$), ppm: 0.88 (3H, m), 1.1–1.5 (16H, m), 1.78 (2H, m), 2.96 (2H, t), 4.04 (3H, s), 6.11 (1H, d, J=1.8Hz), 6.22 (1H, dd, J=1.8Hz and 3.9 Hz), 6.38 (1H, m), 6.86 (1H, dd, J=3.9 and 2.6), 6.97 (1H, m), 7.03 (1H, s), 7.26 (1H, m), 12.6–12.7 (2H, two bs), 12.9 (1H, bs).

By analogous procedure all the compounds prepared in WO 95/17381 can be synthesized and in particular:

4-ethoxy-5-[[5-(undec-10-en-1-yl)-2H-pyrrol-2-ylidene] methyl]-2,2'-bi-1H-pyrrole, hydrochloride, m.p. 80°–97° C.;

4-ethoxy-5-[(5-decyl-2H-pyrrol-2-ylidene)methyl]-2,2'-bi-1H-pyrrole, hydrochloride;

4-ethoxy-5-[(5-dodecyl-2H-pyrrol-2-ylidene)methyl]-2,2'-bi-1H-pyrrole, hydrochloride;

4-ethoxy-5-[(5-phenethyl-2H-pyrrol-2-ylidene)methyl]-2,2'-bi-1H-pyrrole, hydrochloride;

4-ethoxy-5-[[5-(5-phenoxy-pent-1-yl)-2H-pyrrol-2-ylidene] methyl]-2,2'-bi-1H-pyrrole, hydrochloride, m.p.110°–120° C.;

4-ethoxy-5-[(5-tridecyl-2H-pyrrol-2-ylidene)methyl]-2,2'-bi-1H-pyrrole, hydrochloride, m.p. 88°–93° C.;

4-ethoxy-5-[(5-methyl-2H-pyrrol-2-ylidene)methyl]-2,2'-bis-1H-pyrrole, hydrochloride, m.p. 200° C. (dec.);

4-amyloxy-5-[(5-undecyl-2H-pyrrol-2-ylidene)methyl]-2,2'-bi-1H-pyrrole, hydrochloride;

4-undecyloxy-5-[(5-undecyl-2H-pyrrol-2-ylidene)methyl]-2,2'-bi-1H-pyrrole, hydrochloride;

4-undecyloxy-5-[(2H-pyrrol-2-ylidene)methyl]-2,2'-bi-1H-pyrrole, hydrochloride;

4-buthoxy-5-[(5-tridecyl-2H-pyrrol-2-ylidene)methyl]-2,2'-bi-1H-pyrrole, hydrochloride;

4-benzyloxy-5-[(5-tridecyl-2H-pyrrol-2-ylidene)methyl]-2,2'-bi-1H-pyrrole, hydrochloride;

4-buthoxy-5-[[5-(5-phenoxy-pent-1-yl)-2H-pyrrol-2-ylidene] methyl)-2,2'-bi-1H-pyrrole, hydrochloride;

4-benzyloxy-5-[[5-(5-phenoxy-pent-1-yl)-2H-pyrrol-2-ylidene] methyl]-2,2'-bi-1H-pyrrole, hydrochloride;

4-propoxy-5-[(5-undecyl-2H-pyrrol-2-ylidene)methyl]-2,2'-bi-1H-pyrrole, hydrochloride, m.p. 73°–77° C.;

4-butoxy-5-[(5-undecyl-2H-pyrrol-2-ylidene)methyl]-2,2'-bi-1H-pyrrole, hydrochloride, m.p. 81°–83° C.;

4-isopropoxy-5-[(5-undecyl-2H-pyrrol-2-ylidene)methyl]-2,2'-bi-1H-pyrrole, hydrochloride;

4-propoxy-5-[(5-decyl-2H-pyrrol-2-ylidene)methyl]-2,2'-bi-1H-pyrrole, hydrochloride;

4-propoxy-5-[(5-dodecyl-2H-pyrrol-2-ylidene)methyl]-2,2'-bi-1H-pyrrole, hydrochloride;

4-propoxy-5-[[5-(undec-10-en-1-yl)-2H-pyrrol-2-ylidene] methyl]-2,2'-bi-1H-pyrrole, hydrochloride;

4-propoxy-5-[[5-(5-phenoxy-pent-1-yl)-2H-pyrrol-2-ylidene] methyl]-2,2'-bi-1H-pyrrole, hydrochloride;

4-benzyloxy-5-[(5-undecyl-2H-pyrrol-2-ylidene)methyl]2,2'-bi-1H-pyrrole, hydrochloride, m.p. 90°–93° C.;

4-benzyloxy-5-[(2H-pyrrol-2-ylidene)methyl]-2,2'-bi-1Hpyrrole, hydrochloride, m.p. 200°–202° C.;

4-methoxy-5-[[5-(7-cyano-hept-1-yl)-2H-pyrrol-2-ylidene] methyl]-2,2'-bi-1H-pyrrole, hydrochloride;

4-methoxy-5-[[5-(undec-10-en-1-yl)-2H-pyrrol-2-ylidene] methyl]-2,2'-bi-1H-pyrrole, hydrochloride;

4-methoxy-5-[(5-decyl-2H-pyrrol-2-ylidene)methyl]-2,2'-bi-1H-pyrrole, hydrochloride, m.p. 100°–116° C.;

4-methoxy-5-[(5-dodecyl-2H-pyrrol-2-ylidene)methyl]-2,2'-bi-1H-pyrrole, hydrochloride;

4-methoxy-5-[(5-tridecyl-2H-pyrrol-2-ylidene)methyl]-2,2'-bi-1H-pyrrole, hydrochloride, m.p. 80°–100° C.;

4-methoxy-5-[(5-pentadecyl-2H-pyrrol-2-ylidene)methyl]-2,2'-bi-1H-pyrrole, hydrochloride, m.p. 100°–104° C.;

4-methoxy-5-[(5-propyl-2H-pyrrol-2-ylidene)methyl]-2.2'-bi-1H-pyrrole, hydrochloride;

4-methoxy-5-[(5-heptyl-2H-pyrrol-2-ylidene)methyl]-2,2'-bi-1H-pyrrole, hydrochloride, m.p. 140°–145° C.;

4-methoxy-5-[(5-phenethyl-2H-pyrrol-2-ylidene)methyl]-2,2'-bi-1H-pyrrole, hydrochloride, m.p. 170° C. (dec.);

4-methoxy-5-[(5-methyl-4-undecyl-2H-pyrrol-2-ylidene) methyl]-2,2'-bi-1H-pyrrole, hydrochloride;

4-methoxy-5-[(5-propyl-4-undecyl-2H-pyrrol-2-ylidene) methyl]-2,2'-bi-1H-pyrrole, hydrochloride;

4-methoxy-5-[[5-(5-phenoxy-pent-1-yl)-2H-pyrrol-2-ylidene] methyl]-2,2'-bi-1H-pyrrole, hydrochloride, m.p.126°–129° C.;

4-methoxy-5-[(4-ethyl-3,5-dimethyl-2H-pyrrol-2-ylidene) methyl]-2,2'-bi-1H-pyrrole, hydrochloride;

4-methoxy-5-[(4-hexyl-5-methyl-2H-pyrrol-2-ylidene) methyl]-2,2'-bi-1H-pyrrole, hydrochloride;

4-methoxy-5-[(5-nonyl-2H-pyrrol-2-ylidene)methyl]-2,2'-bi-1H-pyrrole, hydrochloride;

4-methoxy-5-[(5-methyl-4-pentyl-2H-pyrrol-2-ylidene) methyl]-2,2'-bi-1H-pyrrole, hydrochloride;

4-methoxy-5-[[5-(5-carboxy-pent-1-yl)-2H-pyrrol-2-ylidene] methyl]-2,2'-bi-1H-pyrrole, hydrochloride, m.p.157°–165° C.;

4-methoxy-5-[[5-(5-carboxy-pent-1-yl)-2H-pyrrol-2-ylidene] methyl]-2,2'-bi-1H-pyrrole, methyl ester, hydrochloride, m.p. 138°–140° C.;

4-methoxy-5-[[5-(6-hydoxy-hex-1-yl)-2H-pyrrol-2-ylidene] methyl]-2,2'-bi-1H-pyrrole, hydrochloride, m.p.118°–121° C.;

4-methoxy-5-[[5-(6-fluoro-hex-1-yl)-2H-pyrrol-2-ylidene] methyl]-2,2'-bi-1H-pyrrole, hydrochloride, m.p.115°–124° C.;

4-methoxy-5-[[5-(5-morpholinecarboxamido-pent-1-yl)-2 H-pyrrol-2-ylidene]methyl]-2,2'-bi-1H-pyrrole, hydrochloride;

4-ethoxy-5-[(5-ethyl-4-pentyl-2H-pyrrol-2-ylidene)methyl] -2,2'-bi-1H-pyrrole, hydrochloride;

4-ethoxy-5-[(5-methyl-4-pentyl-2H-pyrrol-2-ylidene) methyl]-2,2'-bi-iH-pyrrole, hydrochloride;

4-ethoxy-5-[(5-ethyl-4-undecyl-2H-pyrrol-2-ylidene) methyl]-2,2'-bi-1H-pyrrole, hydrochloride;

4-ethoxy-5-[(5-methyl-4-undecyl-2H-pyrrol-2-ylidene) methyl]-2,2'-bi-1H-pyrrole, hydrochloride;

4-ethoxy-5-[(5-heptyl-4-undecyl-2H-pyrrol-2-ylidene) methyl]-2,2'-bi-1H-pyrrole, hydrochloride;

4-propoxy-5-[(5-ethyl-4-undecyl-2H-pyrrol-2-ylidene) methyl)-2,2'-bi-1H-pyrrole, hydrochloride;

4-ethoxy-5-[(4-ethyl-3,5-dimethyl-2H-pyrrol-2-ylidene) methyl]-2,2'-bi-1H-pyrrole, hydrochloride;
4-ethoxy-5-[[5-(5-carboxy-pent-1-yl)-2H-pyrrol-2-ylidene] methyl]-2,2'-bi-1H-pyrrole;
4-propoxy-5-[[5-(5-carboxy-pent-1-yl)-2H-pyrrol-2-ylidene] methyl]-2,2'-bi-1H-pyrrole;
4-ethoxy-5-[[5-(6-hydroxy-hex-1-yl)-2H-pyrrol-2-ylidene] methyl]-2,2'-bi-1H-pyrrole;
4-propoxy-5-[[5-(6-hydroxy-hex-1-yl)-2H-pyrrol-2-ylidene] methyl]-2,2'-bi-1H-pyrrole;
4-propoxy-5-[[5-(11-carboxy-undec-1-yl)-2H-pyrrol-2-ylidene] methyl]-2,2'-bi-1H-pyrrole;
4-propoxy-5-[[5-(12-carboxy-dodec-1-yl)-2H-pyrrol-2-ylidene] methyl]-2,2'-bi-1H-pyrrole;
4-propoxy-5-[[5-(12-hydroxy-dodec-1-yl)-2H-pyrrol-2-ylidene] methyl)-2,2'-bi-1H-pyrrole, hydrochloride;
4-propoxy-5-[[5-(13-hydroxy-tridec-1-yl)-2H-pyrrol-2-ylidene] methyl]-2,2'-bi-1H-pyrrole, hydrochloride;
4-propoxy-5-[[5-(11-cyano-undec-1-yl)-2H-pyrrol-2-ylidene] methyl]-2,2'-bi-1H-pyrrole, hydrochloride;
4-propoxy-5-[[5-(11-carbamoyl-undec-1-yl)-2H-pyrrol-2-ylidene]methyl]-2,2'-bi-1H-pyrrole, hydrochloride;
4-propoxy-5-[[5-(11-ethoxycarbonyl-undec-1-yl)-2H-pyrrol-2-ylidene]methyl]-2,2'-bi-1H-pyrrole, hydrochloride.
4-ethoxy-5-[(5-undecanoyl-2H-pyrrol-2-ylidene)methyl]-2,2'-bi-1H-pyrrole, hydrochloride;
4-ethoxy-5-([5-(11-carboxy-undec-1-yl)-2H-pyrrol-2-ylidene] methyl)-2,2'-bi-1H-pyrrole;
4-ethoxy-5-[[5-(12-carboxy-dodec-1-yl)-2H-pyrrol-2-ylidene] methyl]-2,2'-bi-1H-pyrrole;
4-ethoxy-5-[[5-(12-hydroxy-dodec-1-yl)-2H-pyrrol-2-ylidene] methyl]-2,2'-bi-1H-pyrrole, hydrochloride;
4-ethoxy-5-[[5-(13-hydroxy-tridec-1-yl)-2H-pyrrol-2-ylidene] methyl]-2,2'-bi-1H-pyrrole, hydrochloride;
4-ethoxy-5-[[5-(11-cyano-undec-1-yl)-2H-pyrrol-2-ylidene] methyl]-2,2'-bi-1H-pyrrole, hydrochloride;
4-ethoxy-5-[[5-(11-carbamoyl-undec-1-yl)-2H-pyrrol-2-ylidene] methyl]-2,2'-bi-1H-pyrrole, hydrochloride;
4-ethoxy-5-[[5-(11-ethoxycarbonyl-undec-1-yl)-2H-pyrrol-2-ylidene]methyl]-2,2'-bi-1H-pyrrole, hydrochloride;
4-methoxy-5-[(4,5,6,7-tetrahydro-2H-indol-2-ylidene) methyl]-2,2'-bi-1H-pyrrole, hydrochloride, m.p. 212° C. (dec.);
4-methoxy-5-[(4-hexyl-4,5,6,7-tetrahydro-2H-indol-2-ylidene) methyl]-2,2'-bi-1H-pyrrole, hydrochloride, m.p. 181°–184° C.;
4-ethoxy-5-[(4-hexyl-4,5,6,7-tetrahydro-2H-indol-2-ylidene) methyl]-2,2'-bi-1H-pyrrole, hydrochloride;
4-propoxy-5-[(4-hexyl-4,5,6,7-tetrahydro-2H-indol-2-ylidene) methyl]-2,2'-bi-1H-pyrrole, hydrochloride;
4-ethoxy-5-[[4-(4-carboxy-but-1-yl)-4,5,6,7-tetrahydro-2H-indol-2-ylidene]methyl]-2,2'-bi-1H-pyrrole;
4-ethoxy-5-[(3,5-nonamethylene-2H-pyrrol-2-ylidene) methyl]-2,2'-bi-1H-pyrrole, hydrochloride;
4-propoxy-5-[(3,5-nonamethylene-2H-pyrrol-2-ylidene) methyl]-2,2'-bi-1H-pyrrole, hydrochloride;
4-ethoxy-5-[[4-(4-ethoxycarbonyl-but-1-yl)-4,5,6,7-tetrahydro-2H-indol-2-ylidene]methyl]-2,2'-bi-1H-pyrrole, hydrochloride;
4-ethoxy-5'-methyl-5-[(5-methyl-2H-pyrrol-2-ylidene) methyl-2,2'-bi-1H-pyrrole, hydrochloride, m.p. 180° C. (dec.);
4-propoxy-5'-methyl-5-[(5-undecyl-2H-pyrrol-2-ylidene) methyl]-2,2'-bi-1H-pyrrole, hydrochloride;
4-ethoxy-5'-methyl-5-[[5-(undec-10-en-1-yl)-2H-pyrrol-2-ylidene]methyl]-2,2'-bi-1H-pyrrole, hydrochloride;
4-ethoxy-5'-methyl-5-[(5-decyl-2H-pyrrol-2-ylidene) methyl]-2,2'-bi-1H-pyrrole, hydrochloride;
4-ethoxy-5'-methyl-5-[(5-dodecyl-2H-pyrrol-2-ylidene) methyl]-2,2'-bi-1H-pyrrole, hydrochloride;
4-ethoxy-5'-methyl-5-[(3,5-nonamethylene-2H-pyrrol-2-ylidene) methyl]-2,2'-bi-1H-pyrrole, hydrochloride;
4-ethoxy-5'-heptyl-5-[(5-undecyl-2H-pyrrol-2-ylidene) methyl)-2,2'-bi-1H-pyrrole, hydrochloride;
4-ethoxy-5'-methyl-5-[(5-undecyl-2H-pyrrol-2-ylidene) methyl]-2,2'-bi-1H-pyrrole, hydrochloride;
3-cyano-4-propoxy-5-[(5-undecyl-2H-pyrrol-2-ylidene) methyl]-2,2'-bi-1H-pyrrole, hydrochloride;
3-cyano-4-ethoxy-5-[(5-undecyl-2H-pyrrol-2-ylidene) methyl]-2,2'-bi-1H-pyrrole, hydrochloride;
3-cyano-4-ethoxy-5-[[5-(undec-10-en-1-yl)-2H-pyrrol-2-ylidene]methyl]-2,2'-bi-1H-pyrrole, hydrochloride;
3-cyano-4-ethoxy-5'-methyl-5-[(5-undecyl-2H-pyrrol-2-ylidene)methyl]-2,2'-bi-1H-pyrrole, hydrochloride;
3-ethoxycarbonyl-4-propoxy-5'-methyl-5-[(5-undecyl-2H-pyrrol-2-ylidene)methyl]-2,2'-bi-1H-pyrrole, hydrochloride;
3-ethoxycarbonyl-4-ethoxy-5'-methyl-5-[(5-undecyl-2h-pyrrol-2-ylidene)methyl]-2,2'-bi-1H-pyrrole, hydrochloride,
3-ethoxycarbonyl-4-ethoxy-5'-methyl-5-[[5-undec-10-en-1-yl-2h-pyrrol-2-ylidene]methyl]-2,2'-bi-1H-pyrrole, hydrochloride;
3-methoxycarbonyl-4-methoxy-5'-methyl-5-[(5-undecyl-2h-pyrrol-2-ylidene)methyl]-2,2'-bi-1H-pyrrole, hydrochloride;
3-ethoxycarbonyl-4-ethoxy-5'-methyl-5-[(3,5-nonamethylene-2h-pyrrol-2-ylidene)methyl]-2,2'-bi-1H-pyrrole, hydrochloride;
3-ethoxycarbonyl-4-ethoxy-5'-propyl-5-[(5-undecyl-2h-pyrrol-2-ylidene)methyl]-2,2'-bi-1H-pyrrole, hydrochloride;
3-ethoxycarbonyl-4-propoxy-5'-methyl-5-[[5-(undec-10-en-1-yl)-2h-pyrrol-2-ylidene]methyl]-2,2'-bi-1H-pyrrole, hydrochloride;
3-carboxy-4-propoxy-5'-methyl-5-[(5-undecyl-2h-pyrrol-2-ylidene)methyl]-2,2'-bi-1H-pyrrole;
3-carboxy-4-ethoxy-5'-methyl-5-[(5-undecyl-2h-pyrrol-2-ylidene)methyl]-2,2'-bi-1H-pyrrole;
3-carboxy-4-ethoxy-5'-methyl-5-[[5-(undec-10-en-1-yl)-2h-pyrrol-2-ylidene]methyl]-2,2'-bi-1H-pyrrole; and
3-carboxy-4-ethoxy-5'-propyl-5-[(5-undecyl-2h-pyrrol-2-ylidene)methyl]-2,2'-bi-1H-pyrrole

We claim:

1. A process for the preparation of a 5-[(2H-pyrrol-2-ylidene)methyl]-2,2'-bi-1H-pyrrole compound of formula (I):

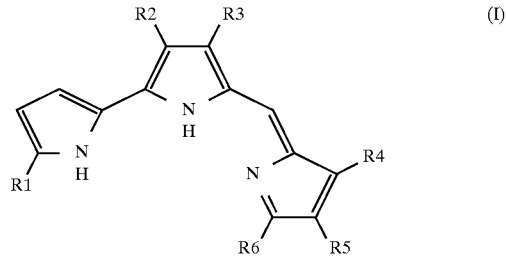

wherein

R1 represents hydrogen, phenyl, $C_1$–$C_{20}$ alkyl or $C_2$–$C_{20}$ alkenyl, wherein the alkyl and alkenyl groups are unsubstituted or substituted by 1 to 3 substituents chosen independently from halogen, $C_1$–$C_6$ alkoxy, hydroxy, aryl and aryloxy;

R2 represents hydrogen, $C_1$–$C_6$ alkyl, cyano, carboxy or ($C_1$–$C_6$ alkoxy)carbonyl;

R3 represents halogen, hydroxy or $C_1$–$C_{11}$ alkoxy unsubstituted or substituted by phenyl;

R4 represent hydrogen, $C_1$–$C_6$ alkyl or phenyl;

each of R5 and R6 independently represents hydrogen, $C_2$–$C_{20}$ alkanoyl, $C_3$–$C_{20}$ alkenoyl, phenyl, $C_1$–$C_{20}$ alkyl or $C_2$–$C_{20}$ alkenyl, wherein the alkanoyl, alkenoyl, alkyl and the alkenyl groups are unsubstituted or substituted by 1 to 3 substituents chosen independently from halogen, $C_1$–$C_6$ alkoxy, hydroxy, aryl, aryloxy, cyano, carboxy, ($C_1$–$C_6$ alkoxy) carbonyl, ($C_3$–$C_4$ alkenyl) carbamoyl, aralkylcarbamoyl, arylcarbamoyl and -CONRcRd in which each of Rc and Rd independently is hydrogen or $C_1$–$C_6$ alkyl or Rc and Rd, taken together with the nitrogen atom to which they are linked, form a morpholino or piperidino ring;

or two of R4, R5 and R6 taken together form a $C_4$–$C_{12}$ polymethylene chain, which are unsubstituted or substituted by a $C_1$–$C_{12}$ alkyl, by a $C_2$–$C_{12}$ alkenyl or by a $C_1$–$C_{12}$ alkylidene group, wherein the alkyl, alkenyl and alkylidene groups are in turn unsubstituted or substituted by a substituent chosen from halogen, $C_1$–$C_6$ alkoxy, hydroxy, cyano, carboxy, ($C_1$–$C_6$ alkoxy)carbonyl, aryloxy and aryl; the remaining one being hydrogen or $C_1$–$C_{12}$ alkyl; and the pharmaceutically acceptable salts thereof;

the process comprising reacting a compound of formula (VIII)

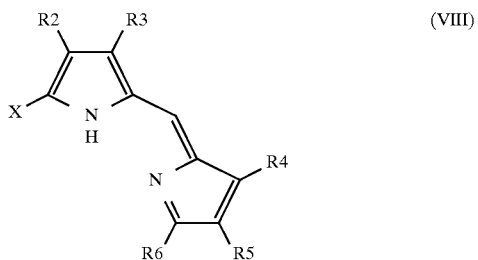

wherein

R2, R3, R4, R5, R6 are as defined above and X is a leaving group, with a compound of formula (IX)

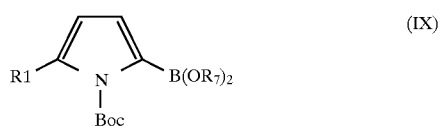

wherein

R1 is as defined above and R7 is hydrogen or a lower alkyl chain;

and, if desired, converting a compound of formula (I) into another compound of formula (I) and/or, if desired, salifying a compound of formula (I) and/or, if desired, converting a salt of a compound of formula (I) into a free compound and/or, if desired, separating a mixture of isomers of a compound of formula (I) into the single isomers.

2. A process according to claim 1, wherein in a compound of formula (VIII) the leaving group X is halogen or a trifluoromethanesulphonate group, in a compound of formula (IX) R7 is hydrogen or a $C_1$–$C_4$ alkyl chain, and the reaction is carried out in an organic solvent, in the presence of a palladium (O) catalyst and of a basic agent.

3. A process according to claim 2, wherein in a compound of formula (VIII) the leaving group X is trifluoromethanesulphonate and the reaction is carried out in dioxane or toluene, in the presence of a Pd(PPh$_3$)$_4$ and sodium or potassium carbonate.

4. A process according to claim 1, wherein in the compound of formula (I):

R1 represents hydrogen, $C_1$–$C_{12}$ alkyl or $C_2$–$C_{12}$ alkenyl, wherein the alkyl and the alkenyl groups are unsubstituted or substituted by aryl or aryloxy;

R2 represents hydrogen, cyano, carboxy or ($C_1$–$C_4$ alkoxy) carbonyl;

R3 represents hydroxy or $C_1$–$C_{11}$ alkoxy unsubstituted or substituted by phenyl;

R4 represents hydrogen or $C_1$–$C_4$ alkyl;

each of R5 and R6 independently represents hydrogen, $C_3$–$C_{14}$ alkyl or $C_3$–$C_{14}$ alkenyl, wherein the alkyl and the alkenyl groups are unsubstituted or substituted by a substituent chosen from halogen, $C_1$–$C_4$ alkoxy, hydroxy, aryl, aryloxy, cyano, carboxy, ($C_1$–$C_4$ alkoxy)carbonyl, aralkylcarbamoyl, arylcarbamoyl and -CONRcRd in which each of Rc and Rd independently is hydrogen or $C_1$–$C_4$ alkyl or Rc and Rd, taken together with the nitrogen atom to which they are linked, form a morpholino or piperidino ring; or two of R4, R5 and R6 taken together form a $C_4$–$C_9$ polymethylene chain, which are unsubstituted or substituted by a $C_1$–$C_6$ alkyl, by a $C_3$–$C_6$ alkenyl or by a $C_1$–$C_8$ alkylidene group, wherein the alkyl, alkenyl and alkylidene groups are in turn unsubstituted or substituted by a substituent chosen from halogen, $C_1$–$C_4$ alkoxy, hydroxy, cyano, carboxy, ($C_1$–$C_4$ alkoxy)carbonyl, aryloxy and aryl; the remaining one being hydrogen or $C_1$–$C_6$ alkyl.

5. A process according to claim 1, wherein the compound of formula (I) is selected from:

4-methoxy-5-[(5-undecyl-2H-pyrrol-2-ylidene)methyl]-2,2'-bi-1H-pyrrole;

4-ethoxy-5-[[5-(undec-10-en-1-yl)-2H-pyrrol-2-ylidene]methyl]-2,2'-bi-1H-pyrrole;

4-ethoxy-5-[(5-decyl-2H-pyrrol-2-ylidene)methyl]-2,2'-bi-1H-pyrrole;

4-ethoxy-5-[(5-dodecyl-2H-pyrrol-2-ylidene)methyl]-2,2'-bi-1H-pyrrole;

4-ethoxy-5-[(5-phenethyl-2H-pyrrol-2-ylidene)methyl]-2,2'-bi-1H-pyrrole;

4-ethoxy-5-[[5-(5-phenoxy-pent-1-yl)-2H-pyrrol-2-ylidene]methyl]-2,2'-bi-1H-pyrrole;

4-ethoxy-5-[(5-tridecyl-2H-pyrrol-2-ylidene)methyl]-2,2'-bi-1H-pyrrole;

4-ethoxy-5-[(5-methyl-2H-pyrrol-2-ylidene)methyl]-2,2'-bis-1H-pyrrole;

4-amyloxy-5-[(5-undecyl-2H-pyrrol-2-ylidene)methyl]-2,2'-bi-1H-pyrrole;

4-undecyloxy-5-[(5-undecyl-2H-pyrrol-2-ylidene)methyl]-2,2'-bi-1H-pyrrole;

4-undecyloxy-5-[(2H-pyrrol-2-ylidene)methyl]-2,2'-bi-1H-pyrrole;

4-buthoxy-5-[(5-tridecyl-2H-pyrrol-2-ylidene)methyl]-2,2'-bi-1H-pyrrole;

4-benzyloxy-5-[(5-tridecyl-2H-pyrrol-2-ylidene)methyl]-2,2'-bi-1H-pyrrole;

4-buthoxy-5-[[5-(5-phenoxy-pent-1-yl)-2H-pyrrol-2-ylidene] methyl)-2,2'-bi-1H-pyrrole;

4-benzyloxy-5-[[5-(5-phenoxy-pent-1-yl)-2H-pyrrol-2-ylidene] methyl]-2,2'-bi-1H-pyrrole;

4-propoxy-5-[(5-undecyl-2H-pyrrol-2-ylidene)methyl]-2,2'-bi-1H-pyrrole;

4-butoxy-5-[(5-undecyl-2H-pyrrol-2-ylidene)methyl]-2,2'-bi-1H-pyrrole;

4-isopropoxy-5-[(5-undecyl-2H-pyrrol-2-ylidene)methyl]-2,2'-bi-1H-pyrrole;

5 4-propoxy-5-[(5-decyl-2H-pyrrol-2-ylidene)methyl]-2,2'-bi-1H-pyrrole;

4-propoxy-5-[(5-dodecyl-2H-pyrrol-2-ylidene)methyll-2,2'-bi-1H-pyrrole;
4-propoxy-5-[[5-(undec-10-en-1-yl)-2H-pyrrol-2-ylidene]methyl]-2,2'-bi-1H-pyrrole;
4-propoxy-5-[[5-(5-phenoxy-pent-1-yl)-2H-pyrrol-2-ylidene] methyl]-2,2'-bi-1H-pyrrole;
4-benzyloxy-5-[(5-undecyl-2H-pyrrol-2-ylidene)methyl]2,2'-bi-1H-pyrrole;
4-benzyloxy-5-[(2H-pyrrol-2-ylidene)methyl]-2,2'-bi-1H-pyrrole;
4-methoxy-5-[[5-(7-cyano-hept-1-yl)-2H-pyrrol-2-ylidene]methyl]-2,2'-bi-1H-pyrrole;
4-methoxy-5-[[5-(undec-10-en-1-yl)-2H-pyrrol-2-ylidene] 30 methyl]-2,2'-bi-1H-pyrrole;
4-methoxy-5-[(5-decyl-2H-pyrrol-2-ylidene)methyl]-2,2'-bi-1H-pyrrole;
4-methoxy-5-[(5-dodecyl-2H-pyrrol-2-ylidene)methyl]-2,2'-bi-1H-pyrrole;
4-methoxy-5-[(5-tridecyl-2H-pyrrol-2-ylidene)methyl]-2,2'-bi-1H-pyrrole;
4-methoxy-5-[(5-pentadecyl-2H-pyrrol-2-ylidene)methyl]-2,2'-bi-1H-pyrrole;
4-methoxy-5-[(5-propyl-2H-pyrrol-2-ylidene)methyl]-2.2'-bi-1H-pyrrole;
4-methoxy-5-[(5-heptyl-2H-pyrrol-2-ylidene)methyl]-2,2'-bi-1H-pyrrole;
4-methoxy-5-[(5-phenethyl-2H-pyrrol-2-ylidene)methyll-2,2'-bi-1H-pyrrole;
4-methoxy-5-[(5-methyl-4-undecyl-2H-pyrrol-2-ylidene)methyl]-2,2'-bi-1H-pyrrole;
4-methoxy-5-[(5-propyl-4-undecyl-2H-pyrrol-2-ylidene)methyl]-2,2'-bi-1H-pyrrole;
4-methoxy-5-[[5-(5-phenoxy-pent-1-yl)-2H-pyrrol-2-ylidene] methyl]-2,2'-bi-1H-pyrrole;
4-methoxy-5-[(4-ethyl-3,5-dimethyl-2H-pyrrol-2-ylidene)methyl]-2,2'-bi-1H-pyrrole;
4-methoxy-5-[(4-hexyl-5-methyl-2H-pyrrol-2-ylidene)methyl]-2,2'-bi-1H-pyrrole;
4-methoxy-5-[(5-nonyl-2H-pyrrol-2-ylidene)methyl]-2,2'-bi-1H-pyrrole;
4-methoxy-5-[(5-methyl-4-pentyl-2H-pyrrol-2-ylidene)methyl]-2,2'-bi-1H-pyrrole;
4-methoxy-5-[[5-(5-carboxy-pent-1-yl)-2H-pyrrol-2-ylidene] methyl]-2,2'-bi-1H-pyrrole;
4-methoxy-5-[[5-(5-carboxy-pent-1-yl)-2H-pyrrol-2-ylidene] methyl]-2,2'-bi-1H-pyrrole, methyl ester;
4-methoxy-5-[[5-(6-hydoxy-hex-1-yl)-2H-pyrrol-2-ylidene] methyl]-2,2'-bi-1H-pyrrole;
4-methoxy-5-[[5-(6-fluoro-hex-1-yl)-2H-pyrrol-2-ylidene] methyl]-2,2'-bi-1H-pyrrole;
4-methoxy-5-[[5-(5-morpholinecarboxamido-pent-1-yl)-2H-pyrrol-2-ylidene]methyl]-2,2'-bi-1H-pyrrole;
4-ethoxy-5-[(5-ethyl-4-pentyl-2H-pyrrol-2-ylidene)methyl]-2,2'-bi-1H-pyrrole;
4-ethoxy-5-[(5-methyl-4-pentyl-2H-pyrrol-2-ylidene)methyl]-2,2'-bi-1H-pyrrole;
4-ethoxy-5-[(5-ethyl-4-undecyl-2H-pyrrol-2-ylidene)methyl]-2,2'-bi-1H-pyrrole;
4-ethoxy-5-[(5-methyl-4-undecyl-2H-pyrrol-2-ylidene)methyl]-2,2'-bi-1H-pyrrole;
4-ethoxy-5-[(5-heptyl-4-undecyl-2H-pyrrol-2-ylidene)methyl]-2,2'-bi-1H-pyrrole;
4-propoxy-5-[(5-ethyl-4-undecyl-2H-pyrrol-2-ylidene)methyl)-2,2'-bi-1H-pyrrole;
4-ethoxy-5-[(4-ethyl-3,5-dimethyl-2H-pyrrol-2-ylidene)methyl]-2,2'-bi-1H-pyrrole;
4-ethoxy-5-[[5-(5-carboxy-pent-1-yl)-2H-pyrrol-2-ylidene] methyl]-2,2'-bi-1H-pyrrole;
4-propoxy-5-[[5-(5-carboxy-pent-1-yl)-2H-pyrrol-2-ylidene] methyl]-2,2'-bi-1H-pyrrole;
4-ethoxy-5-[[5-(6-hydroxy-hex-1-yl)-2H-pyrrol-2-ylidene] methyl]-2,2'-bi-1H-pyrrole;
4-propoxy-5-[[5-(6-hydroxy-hex-1-yl)-2H-pyrrol-2-ylidene] methyl]-2,2'-bi-1H-pyrrole;
4-propoxy-5-[[5-(11-carboxy-undec-1-yl)-2H-pyrrol-2-ylidene] methyl]-2,2'-bi-1H-pyrrole;
4-propoxy-5-[[5-(12-carboxy-dodec-1-yl)-2H-pyrrol-2-ylidene] methyl]-2,2'-bi-1H-pyrrole;
4-propoxy-5-[[5-(12-hydroxy-dodec-1-yl)-2H-pyrrol-2-ylidene] methyl]-2,2'-bi-1H-pyrrole;
4-propoxy-5-[[5-(13-hydroxy-tridec-1-yl)-2H-pyrrol-2-ylidene] methyl]-2,2'-bi-1H-pyrrole;
4-propoxy-5-[[5-(11-cyano-undec-1-yl)-2H-pyrrol-2-ylidene] methyl]-2,2'-bi-1H-pyrrole;
4-propoxy-5-[[5-(11-carbamoyl-undec-1-yl)-2H-pyrrol-2-ylidene]methyl]-2,2'-bi-1H-pyrrole;
4-propoxy-5-[[5-(11-ethoxycarbonyl-undec-1-yl)-2H-pyrrol-2-ylidene]methyl]-2,2'-bi-1H-pyrrole;
4-ethoxy-5-[(5-undecanoyl-2H-pyrrol-2-ylidene)methyl]-2,2'-bi-1H-pyrrole;
4-ethoxy-5-[[5-(11-carboxy-undec-1-yl)-2H-pyrrol-2-ylidene] methyl)-2,2'-bi-1H-pyrrole;
4-ethoxy-5-[[5-(12-carboxy-dodec-1-yl)-2H-pyrrol-2-ylidene] methyl]-2,2'-bi-1H-pyrrole;
5 4-ethoxy-5-[[5-(12-hydroxy-dodec-1--yl)-2H-pyrrol-2-ylidene] methyl]-2,2'-bi-1H-pyrrole;
4-ethoxy-5-[[5-(13-hydroxy-tridec-1-yl)-2H-pyrrol-2-ylidene] methyl]-2,2'-bi-1H-pyrrole;
4-ethoxy-5-[[5-(11-cyano-undec-1-yl)-2H-pyrrol-2-ylidene] methyl]-2,2'-bi-1H-pyrrole;
4-ethoxy-5-[[5-(11-carbamoyl-undec-1-yl)-2H-pyrrol-2-ylidene] methyl]-2,2'-bi-iH-pyrrole;
4-ethoxy-5-[[5-(11-ethoxycarbonyl-undec-1-yl)-2H-pyrrol-2-ylidene]methyl]-2,2'-bi-1H-pyrrole;
4-methoxy-5-[(4,5,6,7-tetrahydro-2H-indol-2-ylidene) methyl]-2,2'-bi-1H-pyrrole;
4-methoxy-5-[(4-hexyl-4,5,6,7-tetrahydro-2H-indol-2-ylidene) methyl]-2,2'-bi-1H-pyrrole;
4-ethoxy-5-[(4-hexyl-4,5,6,7-tetrahydro-2H-indol-2-ylidene) methyl]-2,2'-bi-1H-pyrrole;
4-propoxy-5-[(4-hexyl-4,5,6,7-tetrahydro-2H-indol-2-ylidene) methyl]-2,2'-bi-1H-pyrrole;
4-ethoxy-5-[[4-(4-carboxy-but-1-yl)-4,5,6,7-tetrahydro-2H-indol-2-ylidene]methyl]-2,2'-bi-1H-pyrrole;
4-ethoxy-5-[(3,5-nonamethylene-2H-pyrrol-2-ylidene) methyl]-2,2'-bi-1H-pyrrole;
4-propoxy-5-1(3,5-nonamethylene-2H-pyrrol-2-ylidene) methyl]-2,2'-bi-1H-pyrrole;
4-ethoxy-5-[[4-(4-ethoxycarbonyl-but-1-yl)-4,5,6,7-tetrahydro-2H-indol-2-ylidene]methyl]-2,2'-bi-1H-pyrrole;
4-ethoxy-5'-methyl-5-[(5-methyl-2H-pyrrol-2-ylidene) methyl-2,2'-bi-1H-pyrrole;
4-propoxy-5'-methyl-5-[(5-undecyl-2H-pyrrol-2-ylidene) methyl]-2,2'-bi-1H-pyrrole;
4-ethoxy-5'-methyl-5-[[5-(undec-10-en-1-yl)-2H-pyrrol-2-ylidene]methyl]-2,2'-bi-1H-pyrrole;
4-ethoxy-5'-methyl-5-[(5-decyl-2H-pyrrol-2-ylidene) methyl]-2,2'-bi-1H-pyrrole;
4-ethoxy-5'-methyl-5-[(5-dodecyl-2H-pyrrol-2-ylidene) methyl]-2,2'-bi-1H-pyrrole;
4-ethoxy-5'-methyl-5-[(3,5-nonamethylene-2H-pyrrol-2-ylidene) methyl]-2,2'-bi-1H-pyrrole;
4-ethoxy-5'-heptyl-5-[(5-undecyl-2H-pyrrol-2-ylidene) methyl)-2,2'-bi-1H-pyrrole;

4-ethoxy-5-methyl-5-[(5-undecyl-2H-pyrrol-2-ylidene)methyl]-2,2'-bi-1H-pyrrole;

3-cyano-4-propoxy-5-[(5-undecyl-2H-pyrrol-2-ylidene)methyl]-2,2'-bi-1H-pyrrole;

3-cyano-4-ethoxy-5-[(5-undecyl-2H-pyrrol-2-ylidene)methyl]-2,2'-bi-1H-pyrrole;

3-cyano-4-ethoxy-5-[[5-(undec-10-en-1-yl)-2H-pyrrol-2-ylidene]methyl]-2,2'-bi-1H-pyrrole;

3-cyano-4-ethoxy-5'-methyl-5-[(5-undecyl-2H-pyrrol-2-ylidene)methyl]-2,2'-bi-1H-pyrrole;

3-ethoxycarbonyl-4-propoxy-5'-methyl-5-[(5-undecyl-2H-pyrrol-2-ylidene)methyl]-2,2'-bi-1H-pyrrole;

4-ethoxycarbonyl-4-ethoxy-5'-methyl-5-[(5-undecyl-2H-pyrrol-2-ylidene)methyl]-2,2'-bi-1H-pyrrole;

3-ethoxycarbonyl-4-ethoxy-5'-methyl-5-[[(5-undec-10-en-1-yl-2H-pyrrol-2-ylidene]methyl]-2,2'-bi-1H-pyrrole;

3-methoxycarbonyl-4-methoxy-5'-methyl-5-[(5-undecyl-2H-pyrrol-2-ylidene)methyl]-2,2'-bi-1H-pyrrole;

3-ethoxycarbonyl-4-ethoxy-5'-methyl-5-[(3,5-nonamethylene-2H-pyrrol-2-ylidene)methyl]-2,2'-bi-1H-pyrrole;

3-ethoxycarbonyl-4-ethoxy-5'-propyl-5-[(5-undecyl-2H-pyrrol-2-ylidene)methyl]-2,2'-bi-1H-pyrrole;

3-ethoxycarbonyl-4-propoxy-5'-methyl-5-[[5-(undec-10-en-1-yl)-2H-pyrrol-2-ylidene]methyl]-2,2'-bi-1H-pyrrole;

3-carboxy-4-propoxy-5'-methyl-5-[(5-undecyl-2H-pyrrol-2-ylidene)methyl]-2,2'-bi-1H-pyrrole;

3-carboxy-4-ethoxy-5'-methyl-5-[(5-undecyl-2H-pyrrol-2-ylidene)methyl]-2,2'-bi-1H-pyrrole;

3-carboxy-4-ethoxy-5'-methyl-5-[[5-(undec-10-en-1-yl)-2H-pyrrol-2-ylidene]methyl]-2,2'-bi-1H-pyrrole; and 3-carboxy-4-ethoxy-5'-propyl-5-[(5-undecyl-2H-pyrrol-2-ylidene)methyl]-2,2'-bi-1H-pyrrole; or a pharmaceutically acceptable salt thereof.

6. A compound of formula (VIII)

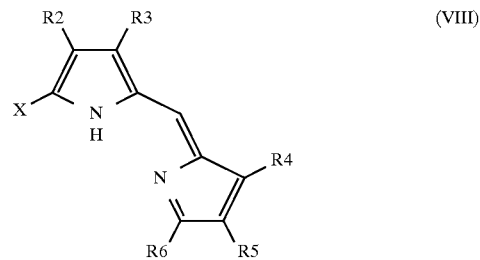

wherein

R2, R3, R4, R5, R6 are as defined in claim 1 and X is a trifluoromethanesulphonate group.

* * * * *